United States Patent
Stephan et al.

(10) Patent No.: US 10,514,344 B2
(45) Date of Patent: Dec. 24, 2019

(54) METHODS OF MONITORING A PROPERTY OF DISPOSABLE DIAGNOSTIC TEST ELEMENTS AND SYSTEMS INCORPORATING THE SAME

(71) Applicant: Roche Diabetes Care, Inc., Indianapolis, IN (US)

(72) Inventors: Peter Stephan, Ilvesheim (DE); Herbert Fink, Mannheim (DE); Stefan Niedermaier, Ladenburg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 475 days.

(21) Appl. No.: 15/263,715

(22) Filed: Sep. 13, 2016

(65) Prior Publication Data

US 2016/0377560 A1 Dec. 29, 2016

Related U.S. Application Data

(63) Continuation of application No. PCT/EP2015/060437, filed on May 12, 2015.

(30) Foreign Application Priority Data

May 14, 2014 (EP) .................... 14168251

(51) Int. Cl.
*G01N 23/223* (2006.01)

(52) U.S. Cl.
CPC ..... *G01N 23/223* (2013.01); *G01N 2223/076* (2013.01); *G01N 2223/303* (2013.01); *G01N 2223/507* (2013.01)

(58) Field of Classification Search
CPC ....... G01N 2223/076; G01N 2223/303; G01N 2223/507; G01N 23/223
See application file for complete search history.

(56) References Cited

U.S. PATENT DOCUMENTS

| 4,162,528 A | 7/1979 | Maldonado et al. |
| 5,657,363 A | 8/1997 | Hossain et al. |
| (Continued) | | |

FOREIGN PATENT DOCUMENTS

| WO | 0184129 A2 | 11/2001 |
| WO | 2007041639 A2 | 4/2007 |
| (Continued) | | |

OTHER PUBLICATIONS

International Search Report, PCT/EP2015/060437; dated Jun. 24, 2015, pp. 1-5.

(Continued)

*Primary Examiner* — Chih-Cheng Kao

(57) ABSTRACT

Methods are provided for producing disposable diagnostic test elements and monitoring a property thereof, where such methods include detecting X-ray fluorescent (XRF) signals of one or more metallic components in a composite of first and second layers applied to a substrate using XRF spectrometry, determining a quantity value for each metallic component in a measured area from the XRF signals, and then calculating an areal coating quantity of the first and the second layers using the quantity values of the metallic components. Additionally or alternatively, the methods can include determining a batch specific code from the XRF signals that can be used when performing a test with a test element. Further provided are systems for monitoring a property of disposable test elements.

14 Claims, 2 Drawing Sheets

(56) References Cited

U.S. PATENT DOCUMENTS

| | | | |
|---|---|---|---|
| 6,036,919 A | 3/2000 | Thym et al. | |
| 6,349,128 B1 * | 2/2002 | Nelson | G01N 23/223 378/44 |
| 6,404,847 B1 * | 6/2002 | Ueki | G01N 23/223 378/44 |
| 6,541,216 B1 * | 4/2003 | Wilsey | C12Q 1/005 435/15 |
| 7,016,462 B1 * | 3/2006 | Keville | G01N 23/223 378/45 |
| 2002/0094058 A1 * | 7/2002 | Kaiser | G01N 23/223 378/45 |
| 2003/0106809 A1 | 6/2003 | Mahyar et al. | |

FOREIGN PATENT DOCUMENTS

| | | |
|---|---|---|
| WO | 2007120552 A2 | 10/2007 |
| WO | 2009033089 A1 | 3/2009 |

OTHER PUBLICATIONS

PCT/EP2015/060437; Written Opinion, dated Jun. 25, 2015, pp. 1-7.
Vrielink J.A.M. et al. 2012, Applicability of X-ray fluorescence spectroscopy as method to determine thickness and composition of stacks of metal thin films: A comparison with imaging and profilometry, Thin Solid Films, Aug. 15, 2011, pp. 1740-1744, vol. 520, No. 6, Elsevier-Sequoia S.A., Lausanne, CH.

* cited by examiner

METHODS OF MONITORING A PROPERTY OF DISPOSABLE DIAGNOSTIC TEST ELEMENTS AND SYSTEMS INCORPORATING THE SAME

CROSS-REFERENCE TO RELATED APPLICATIONS

This patent application is a continuation of Int'l Patent Application No. PCT/EP2015/060437 (filed 12 May 2015), which claims priority to and the benefit of EP Patent Application No. 14168251.8 (filed 14 May 2014). Each patent application is incorporated herein by reference as if set forth in its entirety.

TECHNICAL FIELD

This disclosure relates generally to engineering and medicine/medical diagnostics, and more particularly, it relates methods of producing disposable diagnostic test elements and monitoring a product property of such test elements.

BACKGROUND

Methods are known for producing diagnostic test elements by coating a carrier foil with a bilayer test material structure, which is sequentially coated with a doctor knife as an aqueous suspension. In this context, it is also known to monitor a layer in the wet state by means of an infrared (IR) spectrometer. Only afterwards, the drying of the coating is carried out. IR spectrometry, however, only registers a water content of the coating and not a proportion of functional ingredients. Moreover, only a relative signal is achieved in this way to evaluate the homogeneity of the measured layer within a production batch. A measurement on the final dry product (e.g., a test element) is not possible in such a way.

In the field of semiconductor wafer fabrication, U.S. Pat. No. 5,657,363 discloses using radioisotopic X-ray fluorescence to investigate thin metal films on a semiconductor substrate.

On this basis, an object of this disclosure is to further improve known methods and systems for producing layered, diagnostic test elements including areal coating determination and to provide improved quality control not only when producing test elements but also when using such test elements in an analyte measurement process.

BRIEF SUMMARY

An inventive concept described herein includes using a functional test component of a layered structure as a X-ray fluorescence (XRF)-sensitive reference for a coating quantity. This inventive concept can be incorporated into exemplary methods and systems as described herein and in more detail below.

For example, methods are provided that relate to producing disposable diagnostic test elements, such as blood glucose test strips or tapes and also relate to monitoring a property or quality thereof. The methods can include depositing on a substrate, such as a carrier foil, a first layer of test material including a first metallic component and a second layer of test material covering the first layer and including a second metallic component.

The methods also include detecting XRF signals of the metallic components in the composite of the first and second layer using XRF spectrometry.

The methods also include determining from the XRF signals a quantity value for each metallic component in a measured area. In some instances, the quantity value for each metallic component is determined as a peak value of the XRF signals at a characteristic energy in the XRF spectrum, which simplifies any investigation of the multilayer arrangement of test elements.

The methods also include calculating an areal coating quantity or surface weight of the first and second layer using the quantity values of the metallic components.

In some instances, the metallic components can be at least one of Ti, Mo, Rb, Y, Zr and Hf.

In other instances, and to reduce the expenditure in manufacturing, at least one of the metallic components can be provided in a functional constituent, such as a dye, which is reactive to an analyte when conducting a diagnostic test.

In some instances, predetermined values of a proportion of the first and the second metallic components in the test material can be used for calculating an absolute value of a surface area weight of the first and second layers.

In some instances, at least one of the first and the second metallic components is provided in only one of the first and the second layers to specifically distinguish both layers.

In some instances, the XRF signals are detected through the substrate so that an XRF source and an XRF detector can be oriented towards an uncoated side of the substrate. In this manner, the sensitive test coatings are well-protected during the measurement process, and contamination of the instrument is avoided as well.

In some instances, the XRF signals are taken in a single measurement on both the first and the second layers to avoid adjusting or collimating problems.

In some instances, the XRF signals are calibrated by comparative measurements on one or more comparison elements, where such comparison elements include known amounts of the first or the second metallic components. In this manner, one can avoid quantifying fundamental parameters of individual coating components (e.g., absorption coefficients). In certain instances, a comparison element for the first layer is formed by a thin foil positioned on the substrate and containing the first metallic component. In other instances, a comparison element for the second layer is formed by a thin foil containing the second metallic component and positioned on the first layer which in turn is provided on the substrate.

For further quality improvement of the production process, it is particularly advantageous when the first and second layers are deposited in a coating process, and when a process parameter is adjusted in accordance with the areal coating quantity or surface weight of at least one of the layers.

In some instances, the test materials can be applied as a wet chemistry composition, and XRF signals are detected on a dried chemistry composition thereof to determine a dry surface area weight of the first and the second layers.

Alternatively or additionally, the methods can include determining a batch specific code from the XRF signals, where the batch specific code is configured for obtaining or adjusting a test result from a measurement reading of a test conducted with a diagnostic test element.

In view of the foregoing, systems are provided for monitoring a property of disposable, diagnostic test elements during production that include a means configured for receiving a substrate, such as a carrier foil, upon which is applied a first layer of test material including a first metallic component and a second layer of test material including a second metallic component, where the second layer covers the first layer.

The systems also include a XRF spectrometer configured for detecting XRF signals of the metallic components in the first and the second layers.

The systems also include a processor configured for determining a quantity value for each of the first and the second metallic components in a measured area from the XRF signals, where the processor includes a routine for calculating an areal coating quantity (surface weight) of the first and the second layers using the determined quantity values of the metallic components.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
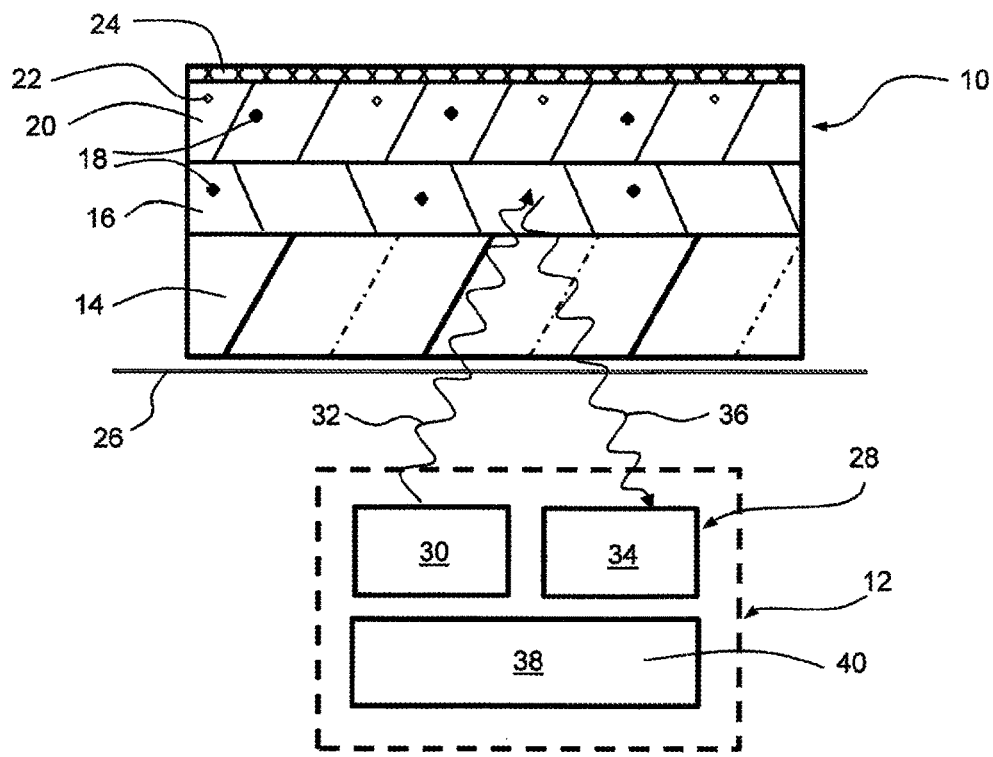
FIG. 1 shows a schematic view of a measuring arrangement including a XRF coating analyzer and a layered test element.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods and systems now will be described more fully hereinafter with reference to the accompanying drawings, in which some, but not all embodiments of the inventive concept are shown. Indeed, the methods and systems may be embodied in many different forms and should not be construed as limited to the embodiments set forth herein; rather, these embodiments are provided so that this disclosure will satisfy applicable legal requirements.

Likewise, many modifications and other embodiments of the methods and systems described herein will come to mind to one of skill in the art to which the disclosure pertains having the benefit of the teachings presented in the foregoing descriptions and the associated drawings. Therefore, it is to be understood that the methods and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

An inventive concept described herein is based on using a functional test component of a layered structure as an XRF-sensitive reference for a coating quantity. Accordingly, methods are provided that relate to producing disposable diagnostic test elements, such as blood glucose test strips or tapes and also relate to monitoring a property or quality thereof. In this way, it is possible to conduct a quantitative analysis of the quality and specifically the surface weight of a continuous bilayer structure of a sandwich-like test element in a contactless measurement without impairing the product and without the need for specific preparation of samples. Advantageously, the measurement is fast and provides a result without further key components that are not functional for the intended diagnostic test.

Methods and Systems

Methods herein that incorporate the inventive concept can include making test elements as well as monitoring a property or quality of such test elements. Likewise, systems also are provided that are configured for monitoring a property of disposable diagnostic test elements during their production.

Briefly, the methods can include depositing on a substrate (14) a first layer (16) of test material including a first metallic component (18) and a second layer (20) of test material covering the first layer (16) and including a second metallic component (22). The methods also can include detecting XRF signals of the metallic components (18, 22) in the composite of the first and second layer (16, 20) using XRF spectrometry. The methods further can include determining a value for the quantity of each metallic component (18, 22) in a measured area from the XRF signals. Moreover, the methods can include calculating the areal coating quantity of the first and second layer (16, 20) using the quantity values of the metallic components (18, 22).

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

FIG. 1 shows an exemplary measuring arrangement that is configured for monitoring an areal coating quantity of a multi-layered, disposable, diagnostic test element 10 by means of a X-ray fluorescence (XRF) analyzer 12.

The test element 10 is generally designed and produced as a two-layered composite on a substrate for detecting an analyte of interest in a body fluid. Such test elements 10 may be provided as intermediate products for application on final goods or may be provided as already finished strip- or tape-like disposables.

The substrate can be formed by a transparent plastic carrier 14 (e.g., a 125 μm thick polycarbonate foil for application as a test strip or a 20 μm thick polyester foil) for application in a test tape.

In the methods, the plastic carrier 14 is coated with a first layer 16 of a reactive test material. This material can include, for example, one or more enzymes, a mediator and dye. The latter reacts by a color change induced by enzymes which are responsive to an analyte, specifically glucose. The dye in the first layer 16 includes a first metallic component 18, which can be also used for product quality monitoring by XRF spectroscopy as outlined below in more detail. In one exemplary composition, the enzyme can be an oxidase or dehydrogenase enzyme are used such as, for example, glucose oxidase or glucose dehydrogenase, and the dye can be molybdenum in the form of phosphomolybdic acid.

In a subsequent method step, the first layer 16 is covered by a second layer 20 of test material containing most of the mediator and the dye which also are present in the first layer 16. Further, the second layer 20 contains white pigments for separating a blood sample and for providing a white background for optical measurement. The white pigments include a second metallic component 22, namely titanium (Ti) in the form of titanium oxide ($TiO_2$). Thus, the second metallic component 22 is only present in the second layer 20, whereas the first metallic component 18 (Mo) is present in both layers 16, 20.

Then, on the upper side of the test element 10, a spreading web 24 can be attached for homogenous and planar distribution of a body fluid sample such as, for example, blood. When conducting a diagnostic test, the blood sample is applied by the user as a droplet from a skin wound.

In the manufacturing methods, the first and second layers 16, 20 are successively deposited as a wet chemistry composition and dried. The wet test material may be applied with a doctor blade coater or squeegee, and drying of the suspension may occur while transporting a web-like substrate/carrier 14 from roll-to-roll. It is immediately apparent that the test sensitivity will depend on the homogeneity and the surface area weight ($g/cm^2$) of the dried first and second layers 16, 20. For monitoring this product property or quality, the XRF analyzer 12 can be employed, as described below. The monitoring allows quality control in the manufacturing methods and adjusting the test evaluation.

As also shown in illustrated in FIG. 1, the XRF analyzer 12 co-operates with receiving means 26, on which the test element 10 is supported at its bottom side of the carrier 14, thereby avoiding direct contact with the test material. The receiving means 26 may be designed as a table or as a measuring chamber that shields the vicinity against X-rays.

The analyzer 12 includes an XRF spectrometer 28 configured for detecting XRF signals of the metallic components 18, 22 in the first and second layer 16, 20. For this purpose, the spectrometer 28 includes a source 30 for short-wavelength X-rays 32 and a detector 34 for fluorescent radiation 36 emitted from excited (metallic) ingredients of the test element 10. Such XRF spectrometers are available as portable devices such as, for example, Niton XL3t Air from Thermo Fisher Scientific, Inc.

To evaluate the measurement signals, an electronic processor 38 is operable to determine a value for the quantity of each metallic component 18, 22 in a measured area. The processor 38 includes a program routine or software 40 for calculating the areal coating quantity (surface weight) of the first and second layer 16, 20.

Figure 2:
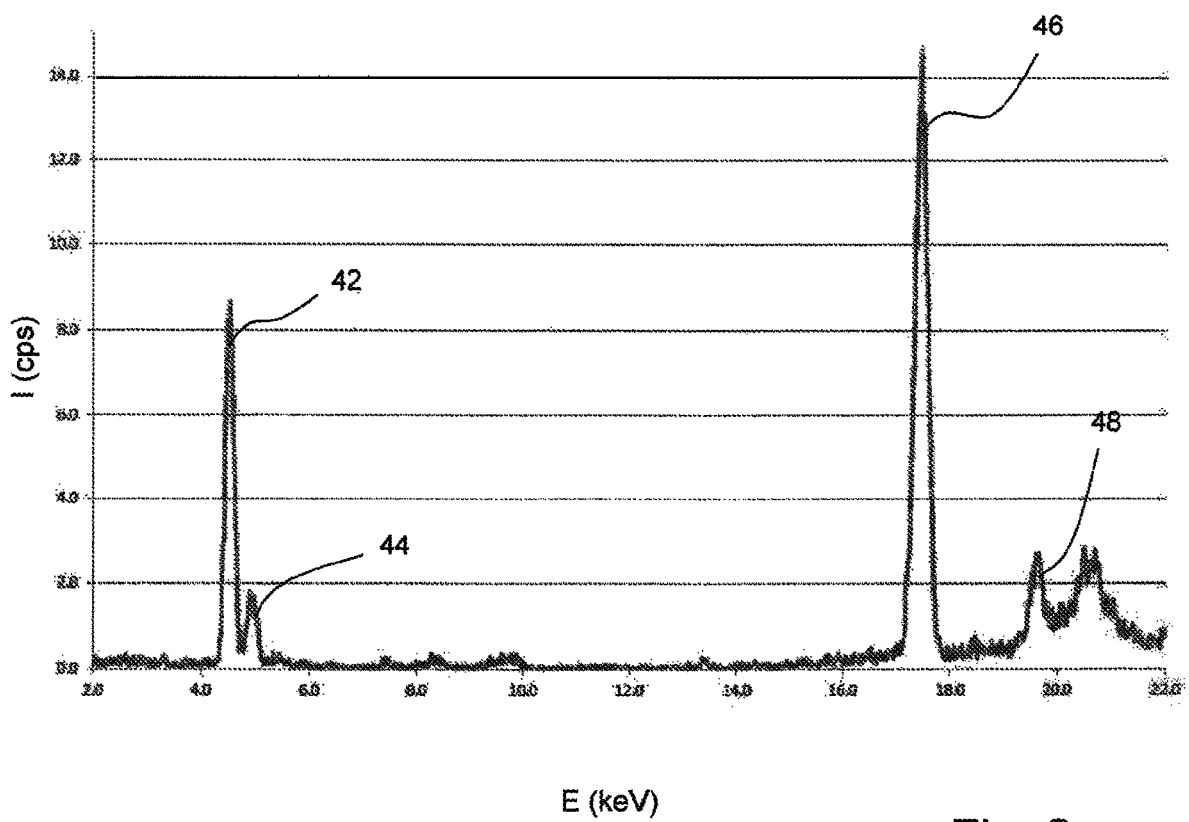
FIG. 2 shows a XRF spectrum plotted with the analyzer of FIG. 1.

FIG. 2 shows an exemplary XRF spectrum obtained from a test element 10, with the intensity (counts per second, cps) plotted over the energy. The spectrum has four distinct peaks, which occur at characteristic energies for each metallic element (e.g., Ti: Kα-line 42 and Kβ-line 44; and Mo: Kα-line 46 and Kβ-line 48). The peak height allows for determining the present quantity of the respective metallic element—provided that a valid calibration has been developed in this application.

Figure 3:
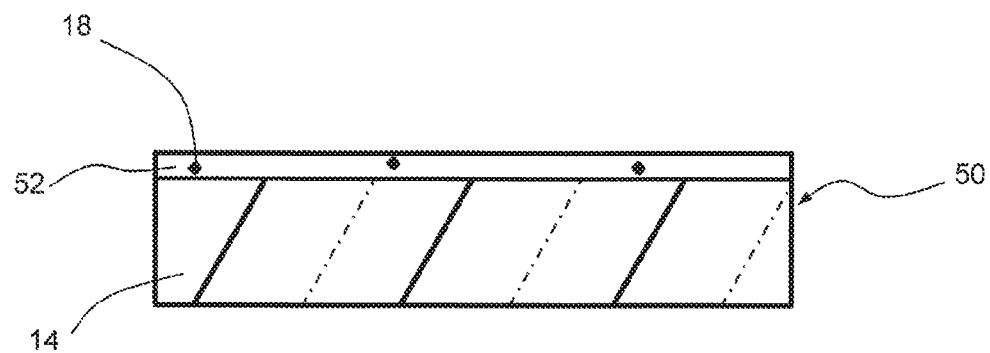
FIGS. 3 and 4 show sectional views of calibration elements for use in the XRF analyzer.

For such purposes, calibration elements that include known amounts of metallic components can be employed. FIG. 3 shows a first exemplary calibration element 50 for comparative measurements that includes the plastic carrier 14 and a thin metal foil 52 made of the first metallic component 18. The foil 52 has an appropriate thickness (i.e., an optimized surface area weight) matched to the expected measurement signal of the test material. For example, a Mo foil of 0.1 μm thickness may be used.

Figure 4:
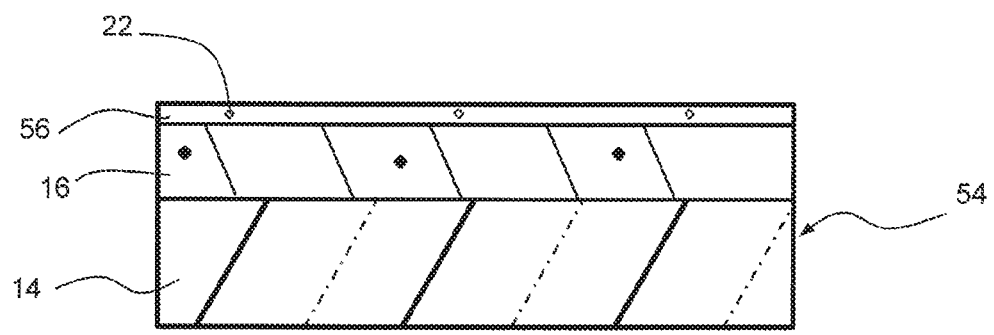

As shown in FIG. 4, an alternative exemplary calibration element 54 is utilized as a reference for the metallic component 22 in the second layer 20. It includes the carrier foil 14, the first layer 16 and a metal foil 56 made of the second metallic component 22. For example, a Ti foil of 3 μm thickness may be used. As Ti is a comparatively lighter element, its XRF signal is attenuated as it travels through the first layer 16, and such attenuation is taken into account by using the calibration element 54 including the layer structure described above. Furthermore, when measuring the calibration elements 50, 54, the spectrometer 28 scans the same surface area as in the measurement on a test element 10.

The calibration allows one to determine a quantity value of each metallic component from the peak value of the XRF signals at the characteristic energy in the XRF spectrum. As explained above, the XRF signals are taken in a single measurement on both layers 16, 20 of a test element 10. Then, the surface area weight of the layers 16, 20 is quantified with the known formulation of the wet coating mass. As the second metallic component 22 (Ti) is only present in the second layer 20, the measured metallic quantity is directly related to the surface area weight of the second layer 20 via the predetermined proportion value in the formulation. By further computation, the surface area weight of the first layer 16 can be determined from the quantity value and the known formulation of the first metallic component 18 (Mo), taking into account the calculated thickness of the second layer 20. Such calculation of the individual dry surface area weight of the first layer and second layer from the XRF reading obtained from a single measurement is exemplified in the following examples.

EXAMPLES

The inventive concept will be more fully understood upon consideration of the following non-limiting examples, which are offered for purposes of illustration, not limitation.

Example 1

The dry surface area weight of titanium and of molybdenum can be calculated, using a predetermined linear calibration function that was obtained as described above with the Ti-foil and the Mo-foil, which gives a dry surface area weight of 4.81 g/m² Ti and of 0.71 g/m² Mo.

The mass fraction of Ti in $TiO_2$ and of Mo in molybdic acid were known from the stoichiometric composition of these compounds and from reference measurements on the raw materials employed. With this mass fraction and stoichiometry, the dry surface area weight of $TiO_2$ and of molybdic acid can be calculated from the dry surface area weight of Ti and Mo, respectively. This gave a dry surface area weight of 8.02 g/m² $TiO_2$ and of 1.36 g/m² molybdic acid.

As $TiO_2$ is only present in the second layer, the dry surface area weight of the second layer then can be determined using the dry surface area weight of $TiO_2$. This is done by using the mass fraction of $TiO_2$ in the dry coating mass of the second layer, known from the recipe of the coating formulation. This gives a dry surface area weight of the second layer of 13.4 g/m².

The mass fraction of molybdic acid in the dry second layer also is known from the recipe of the coating formulation. Thus, the dry surface area weight of molybdic acid in the second layer can now be calculated with the dry surface area weight of the second layer and the mass fraction of molybdic acid in the dry second layer. This gives a dry surface area weight of 1.03 g/m² molybdic acid in the second layer.

This dry surface area weight of molybdic acid in the second layer the was subtracted from the total amount (surface area weight) of molybdic acid present in the two-layered coated sample, to give the dry surface area weight of molybdic acid in the first layer. This gives a dry surface area weight of (1.36 g/m²–1.03 g/m²)=0.33 g/m² molybdic acid in the first layer.

The mass fraction of molybdic acid in the dry first layer was known from the recipe of the coating formulation of the first layer. The mass fraction was used to calculate the dry surface area weight of the first layer. This gave a dry surface area weight of the first layer of 12.18 g/m².

As clearly illustrated by way of this example, the dry surface area weight of the first layer and of the second layer can be both calculated from the XRF values obtained in a single measurement of the two-layered coated sample.

It also is envisaged to adjust the coating process when producing test elements 10 by aid of XRF measurements. For this, samples of test elements 10 can be taken, and process parameters of the coating process such as, for example, the width of a doctor blade gap, can be adjusted in accordance with the areal coating quantity determined on the samples.

Another application contemplates using XRF for determining a batch specific code that is useful when obtaining diagnostic test results signals from measurement readings of a test conducted with the test element 10. Generally, such a code is a mathematical relation between measurement signals (i.e., a remission value in case of photometrical measurements) and the concentration of the analyte (glucose) in the body fluid sample. The remission values are taken at a defined wavelength over a determined time interval. In this context, it is known to provide an empirical code on the basis of reference measurements taken on prepared blood samples with specimen of test elements from a batch. Herein, multivariate generalized linear models may be applied. For example, such a code may be given as a functional relation $$\text{conc}(x)=a+b^{*}x+c^{*}x^{2}+d^{*}x^{e}+f^{*}\exp(x^{g}) \quad \text{Equation (1)}$$

where a, b, c, d, e, f, g are variables determined from the reference measurements, x is the remission and conc is the glucose concentration. Such a code is stored in the glucose meter (e.g., via a batch specific code chip).

When using the XRF monitoring, the reference measurements can be omitted, and the batch specific code is rather calculated from the XRF data (i.e., from the dry areal coating quantity of the functional components Mo and Ti).

In the following, exemplary details are given for code optimization using the XRF values.

In the described application of diagnostic test elements for glucose measurement, a defined mathematical relation can be established between the code function of different batches and the dry surface area weight of the functional components $TiO_2$ and molybdic acid in the coating layer of these batches (and the test elements produced with these batches).

The dry surface area weight of $TiO_2$ and molybdic acid can be measured by the XRF method as described. This allows one to use the code function of a defined batch (e.g., master batch) and the surface area weight values of $TiO_2$ and molybdic acid of an arbitrary batch to calculate the code function for the arbitrary batch and also to directly calculate the results (glucose concentration) from measurements performed with test elements of the arbitrary batch.

In conclusion, an XRF measurement of a fully coated two-layered dry sample (coated foil or test strip) produced a reading for Ti of 23 cps/μA and for Mo of 50 cps/μA.

Example 2

An example of the calculation of the results for measurements with strips of an arbitrary batch is given below:

$$\text{conc}(x)=u+v^{*}\text{conc}(y) \quad \text{Equation (2)}$$

where conc(x) is the glucose concentration measured with test elements of an arbitrary batch, u and v are variables determined with samples from the arbitrary batch (see below), and conc(y) is the glucose concentration obtained from the remission measurement of the arbitrary batch (as described above), but with the code of the master batch.

The variables u and v can be calculated exemplarily with the equations $$u=m+n^{*}(TiO_2)^{p}+o^{*}(MoA) \quad \text{Equation (3)}$$

$$v=r+s^{*}(TiO_2)^{w}+t^{*}(MoA) \quad \text{Equation (4)}$$

where ($TiO_2$) is the dry surface area weight of titanium dioxide in the two-layered coating of test strips of the arbitrary batch, (MoA) is the dry surface area weight of molybdic acid in the two-layered coating of test strips of the arbitrary batch, and m, n, o, p, r, s, t, w are variables determined empirically from several production batches.

In this way, the coding process of new batches can be replaced by XRF measurements of the dry surface area weight of the functional components $TiO_2$ and molybdic acid.

With this procedure, the parameters used for the calculation of the diagnostic result (glucose concentration) are directly derived from the individual test strip used in the measurement. Consequently, the accuracy of the result is significantly improved.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

| Listing of Reference Numbers | |
|---|---|
| 10 | test element |
| 12 | X-ray fluorescence analyzer |
| 14 | carrier/substrate |
| 16 | first layer |
| 18 | first metallic component |
| 20 | second layer |
| 22 | second metallic component |
| 24 | spreading layer |
| 26 | receiving means |
| 28 | X-ray spectrometer |
| 30 | source |
| 32 | short-wavelength X-rays |
| 34 | detector |
| 36 | fluorescent radiation |
| 38 | electronic processor |
| 40 | program routine/software |
| 50 | calibration element |
| 52 | metal foil |
| 54 | calibration element |
| 56 | metal foil |

The invention claimed is:

1. A method of monitoring a property of a disposable diagnostic test element, the method comprising the steps of:
   a. depositing on a substrate, a first layer of test material including a first metallic component and a second layer of test material including a second metallic component, wherein the second layer covers the first layer;
   b. detecting X-ray fluorescent (XRF) signals of the first and the second metallic components in a composite of the first and the second layers by using XRF spectrometry;
   c. determining a quantity value for the first and the second metallic components in a measured area from the XRF signals; and
   d. calculating an areal coating quantity of the first and second layers from the quantity values of the first and the second metallic components and from predetermined values of a proportion of the first and second metallic components.

2. The method of claim 1, wherein at least one of the first and the second metallic components is provided in only one of the first and the second layers.

3. The method of claim 1, wherein the XRF signals are detected through the substrate so that an XRF source and an XRF detector are oriented towards an uncoated side of the substrate.

4. The method of claim 1, wherein the XRF signals are taken in a single measurement on both layers.

5. The method of claim 1 further comprising the step of calibrating the XRF signals by comparative measurements of at least one comparison element including known amounts of the first or the second metallic component.

6. The method of claim 5, wherein a first comparison element for the first layer is formed by a thin foil positioned on the substrate and including the first metallic component.

7. The method of claim 5, wherein a second comparison element for the second layer is formed by a thin foil positioned on the first layer which in turn is provided on the substrate and including the second metallic component.

8. The method of claim 1, wherein the quantity value of the first and the second metallic components is determined as a peak value of the XRF signals at a characteristic energy in a XRF spectrum.

9. The method of claim 1, wherein at least one of the first and the second metallic components is provided in a functional constituent that is reactive to an analyte when conducting a diagnostic test with the test element.

10. The method of claim 9, wherein the functional constituent is a dye.

11. The method of claim 1, wherein the first and the second metallic components comprise an element selected from the group consisting of Ti, Mo, Rb, Y, Zr and Hf.

12. The method of claim 1, wherein the first and the second layers are deposited in a coating process, and wherein a process parameter is adjusted in accordance with the areal coating quantity of at least one of the first and the second layers.

13. The method of claim 1 further comprising the step of applying the first and the second layers as a wet chemistry composition, and detecting XRF signals on a dried chemistry composition thereof to determine a dry surface area weight of the first and the second layers.

14. A system for monitoring a property of a disposable diagnostic test element, the system comprising:
   a. means configured to receive a substrate having applied thereon a first layer of test material including a first metallic component and a second layer of test material covering the first layer and including a second metallic component;
   b. an X-ray fluorescent (XRF) spectrometer configured for detecting XRF signals of the first and the second metallic components in the first and the second layers; and
   c. a processor configured for determining a quantity value for each of the first and the second metallic components in a measured area from the XRF signals, wherein the processor includes a routine for calculating an areal coating quantity of the first and the second layers using the quantity values of the first and the second metallic components and using predetermined values of a portion of the first and second metallic components.

* * * * *